(12) United States Patent
Belardetti et al.

(10) Patent No.: US 7,270,949 B2
(45) Date of Patent: Sep. 18, 2007

(54) FLUORESCENCE BASED T-TYPE CHANNEL ASSAY

(75) Inventors: Francesco Belardetti, Vancouver (GB); Diana Janke, Burnaby (GB); David Parker, Maple Ridge (CA); Terrance P. Snutch, Vancouver (CA)

(73) Assignee: Neuromed Pharmaceuticals Ltd., Vancouver (CA)

( * ) Notice: Subject to any disclaimer, the term of this patent is extended or adjusted under 35 U.S.C. 154(b) by 0 days.

(21) Appl. No.: 10/754,085

(22) Filed: Jan. 7, 2004

(65) Prior Publication Data

US 2004/0180323 A1 Sep. 16, 2004

Related U.S. Application Data

(60) Provisional application No. 60/438,616, filed on Jan. 7, 2003, provisional application No. 60/457,405, filed on Mar. 24, 2003.

(51) Int. Cl.
*C12Q 1/00* (2006.01)
(52) U.S. Cl. ............................................... 435/4
(58) Field of Classification Search ............ 435/4, 435/29, 173.4, 287.1; 436/63
See application file for complete search history.

(56) References Cited

U.S. PATENT DOCUMENTS

| | | | | |
|---|---|---|---|---|
| 5,670,113 | A | * | 9/1997 | Akong et al. .................. 422/63 |
| 6,017,537 | A | * | 1/2000 | Alexander et al. ........ 424/188.1 |
| 6,057,114 | A | * | 5/2000 | Akong et al. ............... 435/7.21 |
| 6,309,858 | B1 | | 10/2001 | Dietrich et al. ............ 435/69.1 |
| 6,358,706 | B1 | | 3/2002 | Dubin et al. ............... 435/69.1 |
| 6,693,172 | B1 | * | 2/2004 | Groppi et al. ............... 530/351 |
| 2001/0041730 | A1 | * | 11/2001 | Li et al. ...................... 514/394 |
| 2002/0045159 | A1 | | 4/2002 | Maher et al. ................... 435/4 |

FOREIGN PATENT DOCUMENTS

| WO | WO98/38301 | | 9/1998 |
|---|---|---|---|
| WO | WO 0073431 | A2 * | 12/2000 |
| WO | WO 01/02561 | | 1/2001 |
| WO | WO 03/019186 | | 3/2003 |
| WO | WO 2004033647 | A2 * | 4/2004 |

OTHER PUBLICATIONS

Voet et al. Biochemistry, 2nd edition, John Wiley & Sons, 1995, pp. 517-519.*
Tweten, RK. Clostridium perfringens beta toxin and *Clostridium septicum* alpha toxin: their mechanisms and possible role in pathogenesis. Veterinary Microbiology, 2001, 82(1): 1-9.*
Klip, A., Insulin stimulation of glucose uptake and the transmembrane potential of muscle cells in culture. FEBS Letters, 1986, 205(1): 11-14.*
(http://www.ncbi.nlm.nih.gov/entrez/query.fcgi?db=gene &cmd=Retrieve&dopt=Graphics&list_uids=8913, updated, Feb. 13, 2005.*
http://www.ncbi.nlm.nih.gov/entrez/query.fcgi?db=gene &cmd=Retrieve&dopt=Graphics&list_uids=3759, updated Jan. 19, 2005.*
http://www.ncbi.nlm.nih.gov/entrez/query.fcgi?db=gene &cmd=Retrieve&dopt=Graphics&list_uids=54207, updated Jan. 19, 2005.*
http://www.ncbi.nlm.nih.gov/entrez/query.fcgi?db=gene &cmd=Retrieve&dopt=Graphics&list_uids=50801, updated Jan. 19, 2005.*
Ishida, H et al. Molecular design and synthesis of artificial ion channels based on cyclic peptides containing unnatural amino acids. J. Org. Chem. 2001. 66: 2978-2989.*
Nelson, DL et al. editors. Lehninger Principles of Biochemistry, 3rd edition. 2000. Worth Publishers: New York. p. 93.*
Carroll, Jr., EJ et al. Ionophore-induced efflux of sodium and potassium ions from sea urchin eggs. 1986. Gamete Research. 14: 355-364.*
Andersson, MA et al. The mitochondrial toxin produced by *Streptomyces griseus* strains isolated from an indoor environment is valinomycin. Applied and Environmental Microbiology. 1998. 64(12): 4767-4773.*
International Search Report for PCT/CA2004/000023, mailed on Jun. 11, 2004, 7 pages.
Lambert et al., Journal of Membrane Biology (1989) 111(2):113-132.
Laris et al., Biochimica et Biophysica Acta (1976) 436(2):475-488.
Bourinet et al., Nature Neuroscience 2:407-415 (1999).
Cribbs et al., Circ. Res. 83:103-109 (1998).
Dunlap et al., Trends Neurosci. 18:89-98 (1995).
Fletcher et al., Cell 87:607-617 (1996).
McCleskey et al., Curr. Topics Membr. 39:295-326 (1991).
McRory et al., J.Biol. Chem. 276: 3999-4011 (2001).
Ophoff et al., Cell 87:543-552 (1996).
Perez-Reyes et al., Nature 391:896-900 (1998).
Stea et al., "Voltage-gated calcium channels." in Handbook of Receptors and Channels, edited by R.A. North, CRC Press (1994).
Zhuchenko et al., Nature Genetics 15:62-69 (1997).

\* cited by examiner

*Primary Examiner*—Leon B. Lankford, Jr.
*Assistant Examiner*—Susan E. Fernandez
(74) *Attorney, Agent, or Firm*—Morrison & Foerster LLP

(57) ABSTRACT

A fluorescence based assay for compounds that modulate T-type calcium ion channels and that can be adapted to high throughput screening formats. Modulators of T-type channels are useful to correct functional abnormalities. These abnormalities are associated with epilepsy, pain, schizophrenia, depression, anxiety, cardiac arrhythmia, hypertension, certain types of cancer, diabetes, infertility, sexual dysfunction and other undesirable conditions.

18 Claims, 5 Drawing Sheets

FLUORESCENCE BASED T-TYPE CHANNEL ASSAY

CROSS-REFERENCE TO RELATED APPLICATIONS

This application claims benefit under 35 U.S.C. § 119(e) of provisional application U.S. Ser. No. 60/438,616 filed Jan. 7, 2003 and U.S. Ser. No. 60/457,405 filed Mar. 24, 2003. The contents of these applications are incorporated herein by reference.

TECHNICAL FIELD

The invention relates to high-throughput assays for calcium channel blockers. More specifically, the invention concerns a fluorescence-based assay that is designed to identify compounds that modulate voltage-dependent, T-type calcium channel activity via high-throughput, automated screening approaches.

BACKGROUND ART

Under resting conditions, intracellular calcium ion concentrations are very low. The rapid entry of calcium into cells is mediated by voltage-gated calcium channels, integral membrane proteins that respond to fast depolarizations of the membrane by transiently and reversibly opening a calcium-selective pore through the cellular membrane. This pore allows the rapid diffusion of calcium ions (the calcium current) from the extracellular medium, down their concentration gradient, to the intracellular space. Higher intracellular concentrations of calcium ions trigger a wide variety of cellular and physiological responses, including excitation-contraction coupling, hormone secretion and gene expression.

Since normal physiological functions are mediated by calcium channels, malfunction of such channels results in a number of disorders. For example, mutations identified in human and mouse calcium channel genes have been found to account for familial hemiplegic migraine, episodic ataxia type 2, cerebellar ataxia, absence epilepsy and seizures. Ophoff, et al., "Familial hemiplegic migraine and episodic ataxia type-2 are caused by mutations in the Ca2+gene CACNL1A4." *Cell* (1996) 87, 543-552; Fletcher, et al., "Absence epilepsy in tottering mutant mice is associated with calcium channel defects." *Cell* (1996) 87, 607-617; and Zhuchenko, et al., "Autosomal dominant cerebellar ataxia (SCA6) associated with small polyglutamine expansions in the $\alpha_{1A}$-voltage-dependent calcium channel." *Nature Genetics* (1997) 15, 62-69.

Indeed, the clinical treatment of some disorders has been aided by the development of therapeutic calcium channel blockers. See, for example, Janis, et al., *Calcium Channels: Their Properties, Functions, Regulation and Clinical Relevance* (1991). CRC Press, London.

Calcium channels have been classified by their electrophysiological and pharmacological properties as T, L, N, P and Q types (for reviews see McCleskey, et al., *Curr. Topics Membr.* (1991) 39:295-326, and Dunlap, et al., *Trends Neurosci.* (1995) 18:89-98). T-type (or low voltage-activated) channels activate at relatively negative membrane potentials and are highly sensitive to changes in resting potential. The L, N and P/Q-type channels activate at more positive potentials and display diverse kinetics and voltage-dependent properties. There is some overlap in biophysical properties of the high voltage-activated channels, consequently pharmacological profiles are useful to distinguish them. L-type channels are sensitive to dihydropyridine (DHP) agonists and blockers, N-type channels are blocked by the *Conus geographus* peptide toxin, ω-conotoxin GVIA, and P-type channels are blocked by the peptide ω-agatoxin IVA from the venom of the funnel web spider, *Agelenopsis aperta*. The Q- and P-type channels appear very similar, and it has been suggested that they result from alternative splicing of a single gene (Bourinet, et al., "Phenotype variants of P- and Q-type calcium channels are generated by alternative splicing of the α1A subunit gene." *Nature Neuroscience* (1999) 2:407-415.

The high voltage threshold calcium channels (L, N and P/Q) are complexes consisting of three distinct subunits ($\alpha_1$, $\alpha_2\delta$ and β) (reviewed by De Waard, et al., *Ion Channels*, Volume 4, (1997) edited by Narahashi, T. Plenum Press, New York). The $\alpha_1$ subunit is the major pore-forming subunit and contains the voltage sensor and binding sites for calcium channel modulators. The $\alpha_2$ subunit is mainly extracellular, and is disulfide-linked to the transmembrane δ subunit, both of which are derived from the same gene and are proteolytically cleaved in vivo. The β subunit is a non-glycosylated, hydrophilic protein with a high affinity of binding to a cytoplasmic region of the $\alpha_1$ subunit. A fourth subunit, γ, is unique to L-type Ca channels expressed in skeletal muscle T-tubules.

Molecular cloning has revealed the cDNA and corresponding amino acid sequences of six different types of $\alpha_1$ subunits corresponding to the high voltage threshold channels ($\alpha_{1A}$, $\alpha_{1B}$, $\alpha_{1C}$, $\alpha_{1D}$, $\alpha_{1E}$ and $\alpha_{1S}$) and four types of β subunits ($\beta_1$, $\beta_2$, $\beta_3$, and $\beta_4$) (reviewed in Stea, A., Soong, T. W. and Snutch, T. P., "Voltage-gated calcium channels." in *Handbook of Receptors and Channels* (1994), edited by R. A. North, CRC Press).

More recently, several $\alpha_1$ subunits corresponding to the low voltage gated T-type calcium ion channel have been cloned. Descriptions of these cloned $\alpha_1$ subunits may be found, for example, in PCT publications WO 98/38301 and WO 01/02561 as well as in U.S. Pat. Nos. 6,309,858 and 6,358,706, all incorporated herein by reference.

The $\alpha_1$ subunits are generally of the order of 2000 amino acids in length and contain 4 internal homologous repeats (domains I-IV) each having six putative alpha helical membrane spanning segments (S1-S6) with one segment (S4) having positively charged residues every third or fourth amino acid. There are a number of splice variant exceptions. Between domains II and III there is a cytoplasmic domain that is believed to mediate excitation-contraction coupling in $\alpha_{1S}$ and which ranges from 100-400 amino acid residues among the subtypes. The domains I-IV make up roughly ⅔ of the molecule and the carboxy terminus adjacent to the S6 region of domain IV is believed to be on the intracellular side of the calcium channel. In the $\alpha_1$ subunits that code for the high voltage-gated channels, there is a consensus motif (QQ-E-L-GY-WI-E) downstream from the domain I S6 transmembrane segment that is a binding site for the β subunit. However, $\alpha_{1G}$, $\alpha_{1H}$ and $\alpha_{1I}$, the only subunits thus far cloned coding for low voltage-gated channels, lack this binding site.

In some expression systems the high threshold $\alpha_1$ subunits alone can form functional calcium channels although their electrophysiological and pharmacological properties can be differentially modulated by coexpression with any of the four β subunits, and their efficiency is enhanced by the presence of $\alpha_2$. On the other hand, in general, the low voltage gated T-type channels generally function quite well when the $\alpha_1$ subunit is present alone. Perez-Reyes, et al., "Molecular characterization of a neuronal low-voltage-activated T-type calcium channel." *Nature* (1998) 391: 896-900; Cribbs, et al., "Cloning and characterization of α1H from human heart, a member of the T-type Ca2+channel gene family." *Circ. Res.* (1998) 83: 103-109 and McRory, et al., "Molecular and functional characterization of a family of rat brain T-type calcium channels." *J. Biol. Chem.* (2001) 276: 3999-4011.

In the T-type $\alpha_1$ subunit, the pore region (P-region) in each of the four structural domains contains a diagnostic amino acid sequence implicated in channel permeability—i.e., the residues glutamate/glutamate/aspartate/aspartate (EEDD). This also distinguishes T-type channels from sodium (Na) channels where the P-region of the channels from the four domains contains the residues aspartate/glutamate/lysine/alanine (DEKA), and from high threshold calcium channels where the corresponding residues are glutamate/glutamate/glutamate/glutamate (EEEE).

The T-type channels are also distinct in that they do not possess an EF-hand calcium binding motif in the region carboxyl to domain IV S6, while all high threshold calcium channels contain a consensus sequence that is closely related to the EF-hand domain found in certain calcium binding proteins.

It is of considerable interest to identify compounds that modulate channel activity, for example, by blocking the flow of calcium and/or inhibiting the activation of calcium channels. One standard method to do so is through the use of patch clamp experiments. In these experiments, cells must be evaluated individually and in sequence by highly skilled operators, by measuring the calcium current across the cell membrane in response to changes of the membrane potential and/or application of test compounds. These experiments, while valid and informative, are very time consuming and not adaptable to high-throughput assays for compounds that modulate calcium ion channel activity.

For high-throughput assays of high voltage-gated calcium channel blockers, a more efficient assay is currently used which takes advantage of commercially available fluorophores that change their fluorescence emission in the presence of calcium ion. After loading cells expressing high voltage-gated calcium ion channels with such fluorophores, a single operator can measure calcium channel activity in hundreds of wells in parallel by exposing the cells to high levels of extracellular potassium ion. This simple technique is based on the observation that the resting potential of the cells is largely determined by the ratio of the extracellular versus the intracellular potassium ion concentrations. Normally, potassium is lower extracellularly than intracellularly, and produces a resting potential that is negative inside the cell. Increased levels of extracellular potassium, at concentrations close to that present intracellularly, will depolarize the membrane (abolishing the internal negativity), and activate calcium channels. Less activation of calcium channels will be observed if a blocker is applied to the cells.

It is known that calcium channels (and voltage-gated ion channels in general) can exist in three states: inactivated (not available for opening), resting (available for opening), and activated (open). Based on this pattern, in order for the calcium ion channels to respond to the potassium pulse, a substantial fraction of channels must be in the resting state, as opposed to the inactivated state. Typically, at the spontaneous resting membrane potential of −30 mV, about 40-70% of N-type calcium channels are in the resting state and available for opening. It is important to consider that transitions between each of these states is regulated by the membrane voltage. Moreover, the transition from inactivated state to resting state is slow, but the conversion of a resting to an activated channel, where the activated channel allows calcium ion influx, is quite fast. The return of the activated channels to the inactivated form is also relatively slow.

If a compound is successful in blocking calcium channel activation, calcium influx does not occur or occurs to a lesser extent and the fluorescence reading is lower or nonexistent, so this phenomenon can be used to identify modulators.

Attempts to perform this type of assay using low voltage-activated calcium channels (T-type) have not been successful in view of their inactivated status at the spontaneous membrane potential of −30 mV. At this potential, essentially all T-type channels are inactivated, and thus unavailable for activation by a high potassium pulse, or by any physiological stimulus. It has now been found that the fluorescence-based assay described above can be adapted to the T-type channel requirements by decreasing the membrane potential to about −70 mV before potassium ion activation, thus converting a sufficient number of T-type channels to the resting state.

DISCLOSURE OF THE INVENTION

A high-throughput, fluorescence-based assay has been developed that is useful in screening for and identifying compounds that modulate the activity of low-threshold voltage gated T-type calcium channels. The assay functions by modulating the membrane potential in advance of potassium ion activation to convert low voltage activated T-type channels from the inactivated, unavailable state to the resting state, so that they can be subsequently activated by application of high extracellular potassium. In part, the membrane potential is lowered by treating cells expressing the T-type channels with gramicidin or similarly functional compounds that insert into the cell membrane and function as a pores selective for monovalent, positively charged ions. Treatment of the cells with gramicidin alone would not alter the membrane potential, because both potassium ions (which are at high concentration intracellularly) and sodium ions (which are at higher concentrations extracellularly) would flow in opposite directions through gramicidin pores. However; by replacing the sodium ion in the extracellular solution with a large, positively-charged molecule, such as N-Methyl-D-Glucamine(NMDG), which cannot permeate the gramicidin-induced channel, the compensating influx of sodium ions is prevented and the efflux of potassium ions results in a drop in membrane potential sufficient to convert the T-type channels from their inactivated state to their resting state. These channels are then susceptible to activation with high potassium concentration, providing a mechanism for generating a fluorescent signal dependent upon an increase in internal calcium ion concentration through T-type calcium channel activation (in the absence of test compound). Thus, in one aspect, the invention is directed to a method to detect the activation of T-type calcium ion channels. The method comprises treating cells that express at least the $\alpha_1$ subunit of a T-type calcium channel with sufficient potassium ion to activate the T-type channel and measuring the fluorescence emitted by such cells, wherein the cells have been modified to contain a fluorophore that fluoresces in the presence of calcium ion, and wherein said cells have been treated, prior to the potassium ion pulse, with gramicidin in the presence of an isotonic solution of NMDG.

In another aspect, the invention is directed to a method to identify compounds which inhibit the activation of T-type calcium ion channels or block the flow of calcium ion therethrough, which method comprises performing the above described method in the presence and absence of a test compound and determining the ability of the test compound to decrease the level of fluorescence emitted, thereby identifying such compound as able to inhibit the activation of the T-type calcium channel or the flow of calcium ion therethrough. Of course, for any compound that might activate and enhance the flow of calcium ion through the channel, the fluorescence will increase. Thus, the assay can also identify compounds that effect a greater influx of calcium into the cells. Such a result may, in some cases, be desirable.

In other aspects, the invention is directed to kits useful for the performance of the assay and to methods to assess the results for validity.

MODES OF CARRYING OUT THE INVENTION

Figure 1:
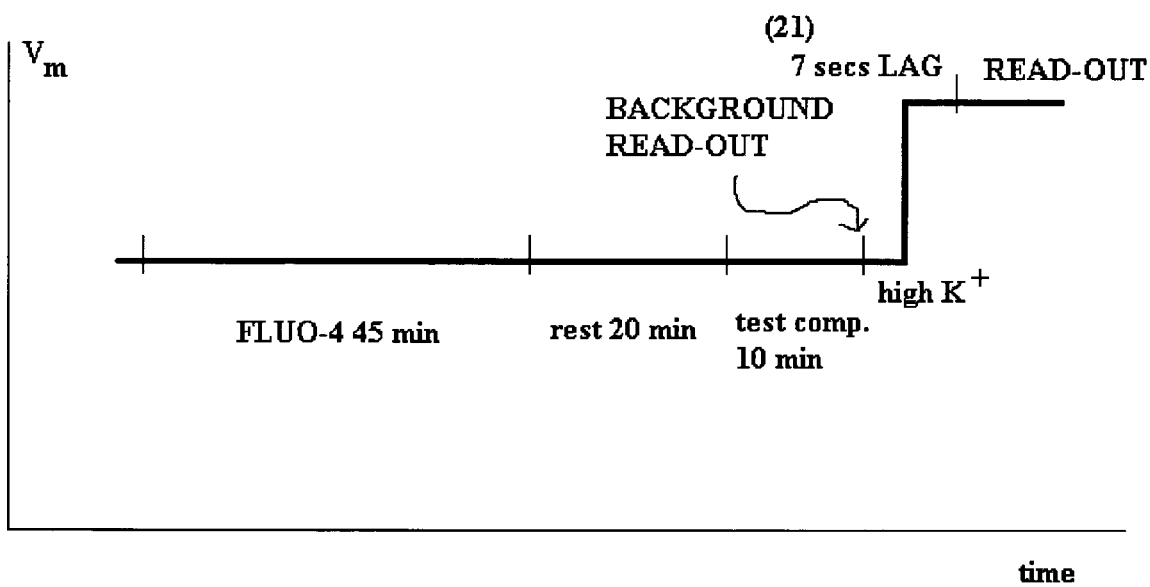
FIG. 1 is a diagram of the voltage patterns over time for a standard N-type assay using intracellular fluorescence.

The invention offers the opportunity to identify compounds that will block either the activation of T-type calcium ion channels or the flow of calcium ion across these channels by comparing the fluorescence of cells containing a fluorophore that responds to calcium ion concentration in the presence and absence of a test compound. The ability of the test compound to decrease the level of fluorescence indicates its abilities to inhibit a T-type calcium channel. Conversely, compounds that enhance the fluorescence are shown to be activators of these channels.

This general type of assay has successfully been applied to high voltage-gated calcium ion channels, typified by N-type channels. It is possible to do this because the membrane potential across the cellular membrane of typically cultured cells such as HEK 293 suspended in isotonic buffer is of the order of –20 mV. At this membrane potential, the majority of high threshold calcium ion channels are in a resting state which is susceptible to activation in a fast reaction in response to high concentrations of potassium ions supplied to the suspending buffer. Thus, cells expressing a high-threshold channel that have been treated with a fluorophore and allowed to internalize it will fluoresce when treated with a sufficient concentration of potassium ion to alter the membrane potential to about 0 mV, thus activating these channels and permitting the flow of calcium into the cells. The interaction of the calcium ion with the fluorophore results in a fluorescence readout which shows that the calcium ion channels have been activated. If this process is conducted in the presence and in the absence of a compound to be tested, the differences in fluorescence output indicates the effect of the compound on the activity of the calcium ion channel.

The ambient membrane potential of cells suspended in isotonic buffer is approximately –20 mV. In contrast to high voltage gated calcium channels, this is a membrane potential at which the low-voltage threshold T-type calcium channels are in an inactivated state and not available for rapid activation. Thus, even in the absence of a blocker compound, no substantial fluorescence occurs.

The applicants have found that by artificially lowering the membrane potential to about –70 mV, the T-type channels can be converted to a resting state from an inactivated state and are thus susceptible to activation by rapid addition of sufficient potassium ion to abruptly increase the membrane potential to around 0 mV. The level of potassium ions required is between 1-100 mM, preferably between 5-70 mM, and more preferably between 20-30 mM. This permits influx of calcium ions through the T-type channels and provides a fluorescence signal, which can then be modulated by the presence of compounds to be tested for their ability to interact with the T-type channel.

The lowering of the membrane potential is achieved by inserting into the membrane itself an artificial, exogenous pore, that permits the influx and efflux of singly charged cations. Upon opening this channel, potassium ions flow out, and typically, sodium ions flow into the cell; thus no substantial net change in membrane potential is effected. However, by concomitantly replacing the sodium ions in the isotonic buffer with a compensating moiety that is unable to permeate the pore, there is a net outflow of potassium ions, resulting in a highly negative membrane potential, sufficient to convert the inactivated T-type channels to the resting state.

Thus, two additional components are required for the assay—a material that will open a channel for monovalent cations and a component which will balance the osmolality of the intracellular environment, but which will not permeate the channel.

Suitable compounds which will insert into the membrane a pore with the desired properties (monovalent cation-selective) include but are not limited to gramicidin (see Wallace, Common structural features in gramicidin and other ion channels. *Bioessays*, 22:227-234, 2000, artificial ion channels such as certain cyclic peptides containing unnatural amino acids (see Ishida, et al., Molecular design and synthesis of artificial ion channels based on cyclic peptides containing unnatural amino acids. *J. Org. Chem.*, 66:2978-2989, 2001) and certain bacterial toxins (see Shatursky, et al., *Clostridium perfrigens* beta-toxin forms potential-dependent, cation-selective channels in lipid bilayers. *Infection and Immunity*, 68:5546-5551, 2000). Lowering the membrane potential of the cells may also be achieved by the stable coexpression of a potassium channel, for example, but not exclusively, IRK-1, TASK-1, TASK-3, TREK-1, TREK-2 and TRAAK. Cells are transfected with the IRK-1 channel and are subsequently selected for cell lines expressing the IRK-1 channel that have a membrane potential of less than –70 mV. Cells stably expressing IRK-1 are subsequently transfected with the T-type channel, then selected for cell lines coexpressing both IRK-1 and the T-type channel with a resting membrane potential of –70 mV, thus favouring a shift of the T-type channels from an inactivated state to a resting state. By increasing the external potassium concentration, the T-type channels are activated allowing for calcium influx resulting in a fluorescence emission upon binding to the fluorophore.

Typical compounds which will balance osmotic pressure, but do not permeate the gramicidin or other artificial pore include for example, N-methyl-D-Glucamine(NMDG), choline, tris[hydroxymethyl]aminomethane (TRIS) and tetra-ethyl-ammonium (TEA).

Alternatively, lowering the membrane potential of the cells may also be achieved by the stable coexpression of a potassium channel, for example, but not exclusively, human IRK-1, TASK-1, TASK-3, TREK-1, TREK-2 and TRAAK. For example, cells are transfected with an expression system for the hIRK-1 channel and selected for cell lines stably expressing the IRK-1 channel that have a membrane potential of less than −70 mV. These cells are then transfected with an expression system for the T-type channel, and selected for cell lines coexpressing both IRK-1 and the T-type channel with a resting membrane potential of −70 mV, thus favoring a shift of the T-type channels from an inactivated state to a resting state. By increasing the external potassium concentration, the T-type channels are activated allowing for calcium influx resulting in a fluorescence emission upon binding to the fluorophore.

Also essential for the conduct of the assay is a suitable fluorophore. The fluorophore must be activated (or inactivated) by the presence of calcium ion. The fluorophore should also be membrane permeable so that cells treated with the fluorophore can assimilate the compounds. Suitable fluorophores include FLUO-4 as well as FLUO-3, FURA, Oregon Green and Calcium Green.

In a typical standard assay using mammalian cells expressing a cloned high-threshold calcium channels, known in the art and shown in FIG. 1, cells are first treated with the fluorophore, such as FLUO-4 for enough time to permit entry of the fluorophore across the membrane, e.g., about 45 minutes, and then washed and allowed to rest for about 20 minutes to equilibrate the intracellular distribution of the fluorescent dye. If a compound is to be added for testing of block or activation, this is then added and allowed to equilibrate for about 10 minutes. The cells are then activated with a concentration of potassium ions which causes the membrane potential to increase from about −20 mV to 0 mV, essentially effecting the flow of calcium into the cell. The fluorescence is then determined using standard methods.

Figure 2:
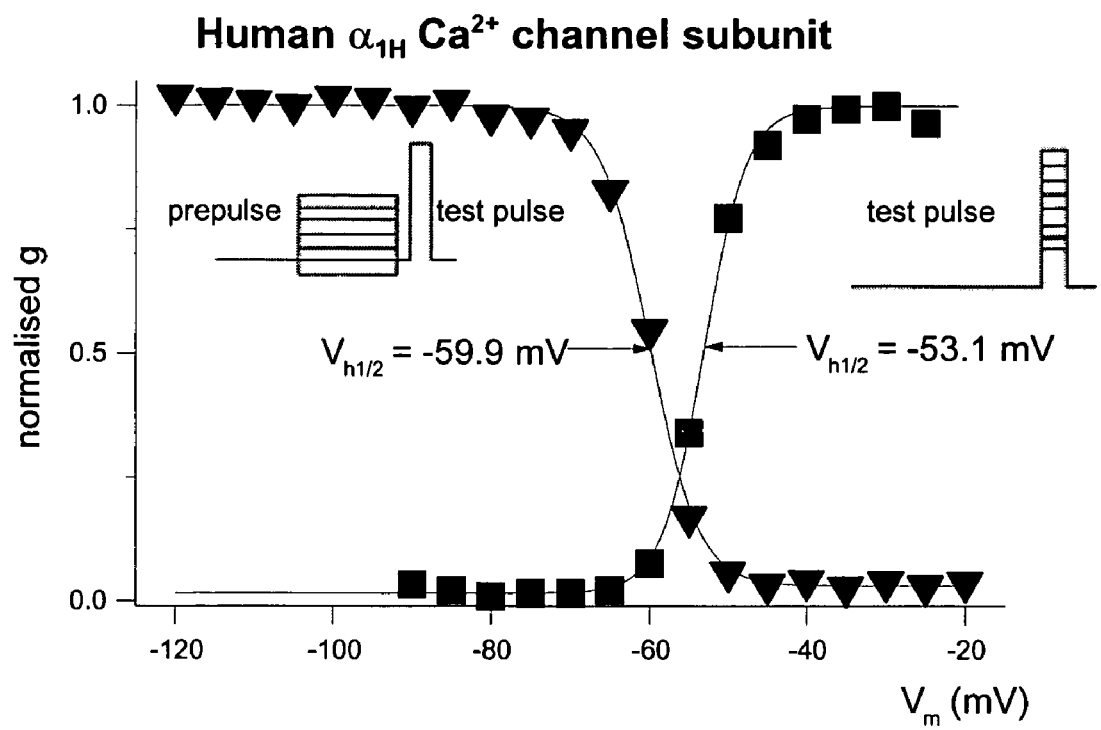
FIG. 2 shows the activation and inactivation curves for two mammalian T-type $\alpha_1$ subunits.
Figure 2:
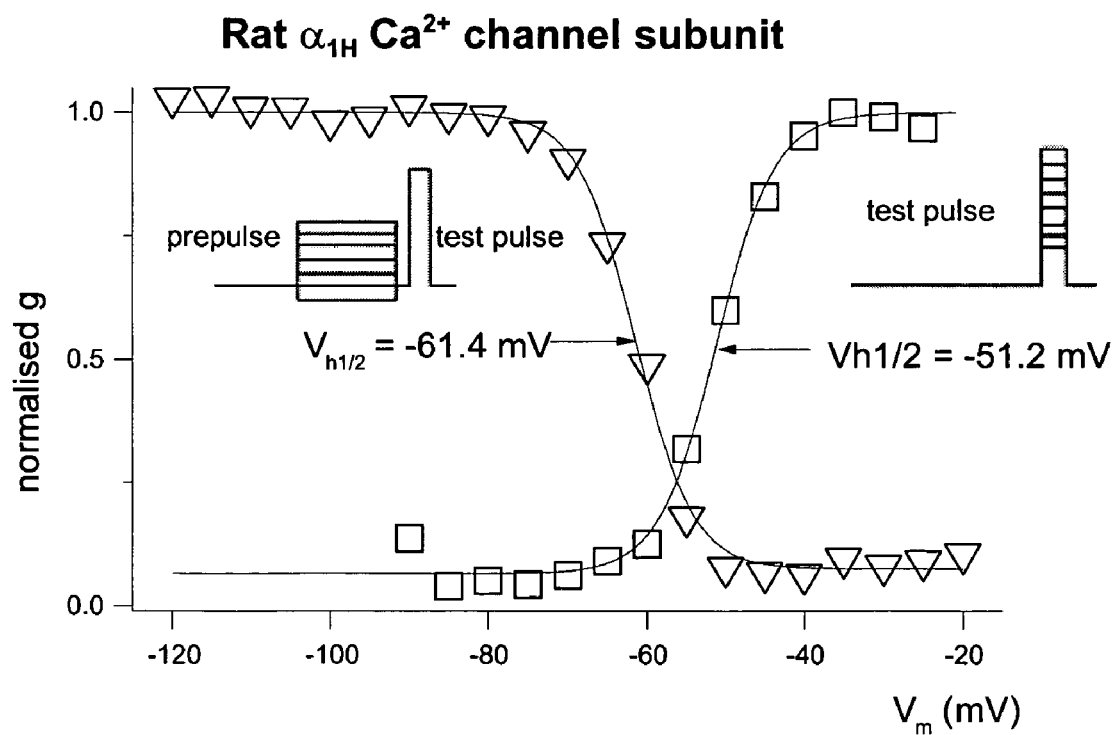

However, as shown in FIG. 2, human and rat T-type $\alpha_1$ subunits are activated at a much lower potential. FIG. 2 shows activation and inactivation as a function of voltage. T-type currents were evoked by applying, every 15 seconds, square test pulses (50 ms duration) from a −110 mV holding potential. In the inactivation curves (triangles) the test pulse was fixed (−40 mV) and the size of the prepulse (1s) varied to the indicated values. In the activation curves, the size of the test pulse was changed to the indicated values. The external solution contained 1 mM calcium ion. In the graphs in FIG. 2, the x-axis plots the membrane voltage of a cell which is expressing the channel subunit and the y-axis plots the fraction of such channels that are in the resting state and available for activation. As shown, the transition from the inactive to activated state occurs in the range of 60 mV to −50 mV.

Figure 3:
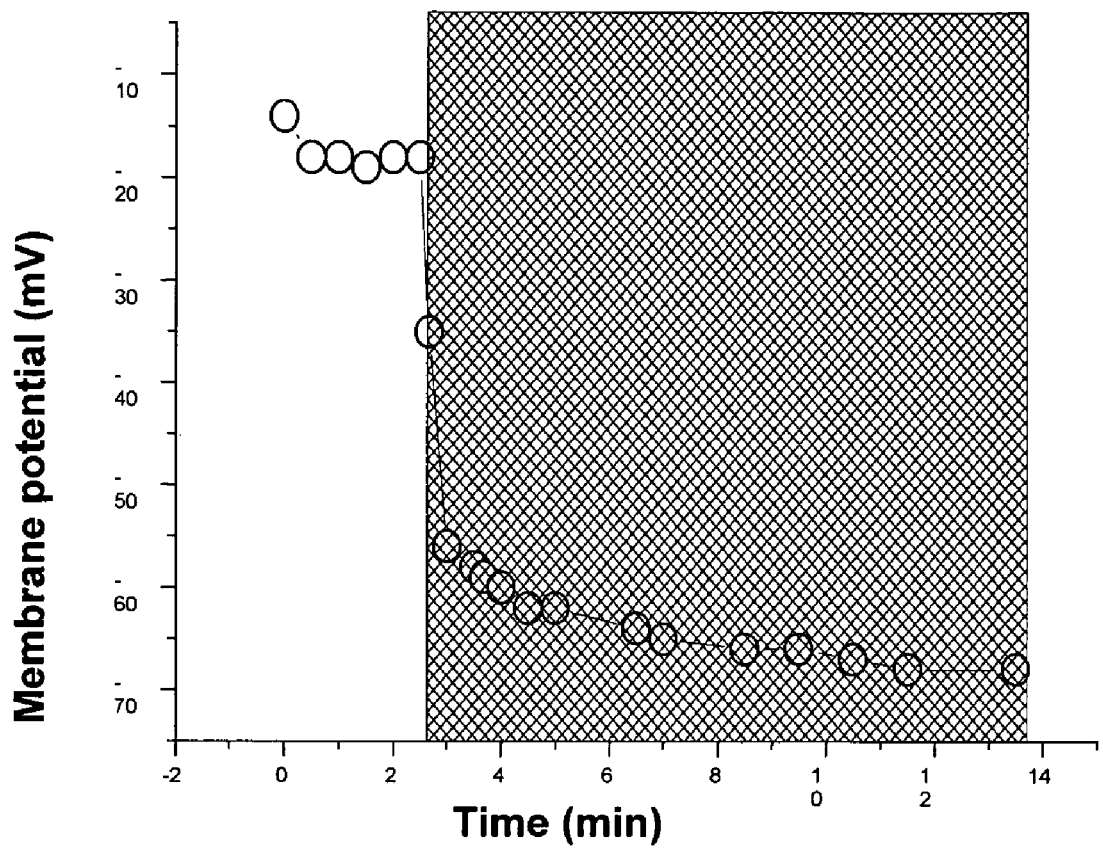
FIG. 3 shows the ability of gramicidin in the presence of NMDG to dramatically lower the membrane potential across a cellular membrane.

FIG. 3 shows that the membrane potential of cells can be altered in the presence of gramicidin when the suspending buffer is maintained isotonic with the intracellular medium by substituting NMDG for external sodium. As shown, when 5 μg/ml gramicidin is added in the absence of external sodium, the membrane potential decreases to about −70 mV.

Figure 4:
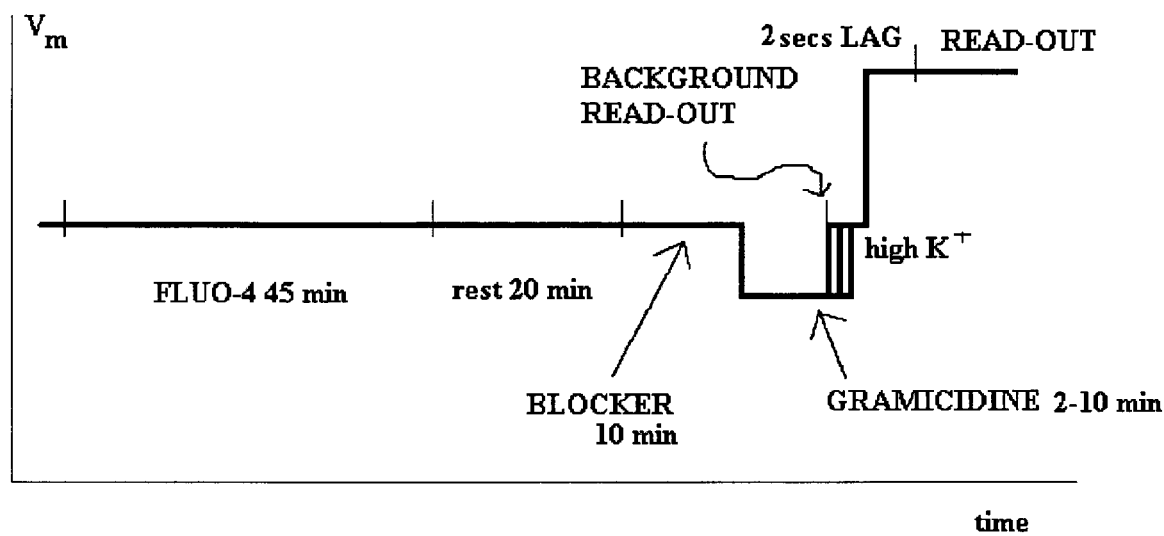
FIG. 4 shows a diagram of the membrane potential variation over time for a fluorescence based assay of T-type calcium channels.

FIG. 4 shows the manner in which the phenomenon in FIG. 3 is used to adapt the assay of FIG. 1. The initial steps in the assay are similar to those of FIG. 1; however, the assay is conducted in an isotonic solution where sodium ion is replaced with NMDG and after the test compound is added and allowed to incubate for about 10 minutes, gramicidin is added and permitted to equilibrate for approximately 2 minutes. After the gramicidin treatment, which lowers the membrane potential to about −70 mV, a pulse of potassium ion quickly alters the membrane potential to zero (0) mV inducing the activation of the T-type channels and an increase in intracellular calcium is detected through a change in fluorescence.

Those compounds that successfully modulate the activity of the T-type channels according to the assays of the invention are useful candidates as pharmaceuticals in the treatment of a variety of conditions which are known to be mediated by inappropriate activity of the T-type channels. As calcium ion signaling is highly significant in a multiplicity of metabolic pathways, the conditions affected are numerous. As used herein, the term "treatment" refers to any pharmacological intervention which results in or has the potential to result in at least an amelioration of the negative effects of the condition. Complete "cure" or complete "prevention" is neither necessary nor realistic.

Among the conditions impacted by the activity of human T-type channels are those associated with the neural system such as epilepsy, depression, schizophrenia, and muscle-related disorders that are controlled by the excitation/relaxation rhythms imposed by the neural system such as cardiac rhythm and other disorders of the cardiovascular system. Also impacted are conditions related to proliferation of cells such as vasodilation or vasorestriction and blood pressure. The activity of calcium ion T-type channels also affects conditions of the genital/urinary system including disorders of sexual function and fertility as well as adequacy of renal function. Other indications include responsivity to anesthetics and Parkinson's disease. That these conditions (and others) are related to T-type channel activity is well known in the art.

The following examples are intended to illustrate but not to limit the invention.

Preparation A

Construction of Stable Cell Lines Expressing Mammalian $\alpha_1$ Subunits of T-Type Calcium Channels Mammalian cell lines stably expressing $\alpha_1$ subunit of T-type calcium channels were constructed by transfecting $\alpha_1$ calcium channel subunit DNA into HEK 293 cells and selecting for antibiotic resistance. Briefly, a full-length T-type calcium channel $\alpha_1$ subunit was subcloned into an expression vector with a selectable marker, pcDNA3 (InvitroGen, San Diego, Calif.). The vector was transfected into HEK 293 cells by lipofection and the cells incubated for 16-20 hours. The cells were fed nonselective medium and incubated for an additional 24 hours, then trypsinized and plated at low density in selective medium supplemented with Geneticin (G418) at a concentration of between 600 to 800 μg/ml. After 12 to 16 days in selective medium, cells which were resistant to G418 were visible and were picked as isolated colonies using a pipet tip technique. After growing up each isolated colony to confluency to establish cell lines, the expression of T-type calcium channels was determined by Northern and Southern blotting.

The funtional confirmation of T-type calcium channels as functional in stably transfected cells was examined electrophysiologically, by either whole patch clamp or single channel analysis, or both.

EXAMPLE 1

Assay for T-type Modulators

The transfected HEK 293 cells prepared in Preparation A were plated in 384-well poly-D-lysine coated micro-well plates at about $1.1 \times 10^5$ cell/well and incubated at 37° C. for about 24 hours and then at 29° C. for about 18 hours.

The cells were then washed with MKH buffer using Bio-tek ELX405 Select plate washer to remove media; the residual volume of buffer is 15 µl/well.

Each well was then treated with fluorescence dye solution containing a mixture of 50 µg FLUO-4 AM (Molecular Probes, F-14201); 45.5 µl DMSO; 45.5 µl 20% Pluronic F-127 (Molecular Probes, P-6867) and 4 ml MKH buffer. After incubation at 29° C. for 45 minutes, the cells were washed with EB buffer as described above so that the solution is fully replaced, and the cells were then incubated at 20° C. for 10 minutes.

To each well, EB buffer was added also containing DMSO at a concentration equal to that of the test compounds for negative controls, the known blocker penfluoridol at 2.5 µM for positive control, and test compounds (diluted in DMSO) for experimental wells. The cells were then incubated at room temperature for another 10 minutes and put onto a Fluoroskan Ascent microplate reader. Background fluorescence was read in all wells.

Figure 5:
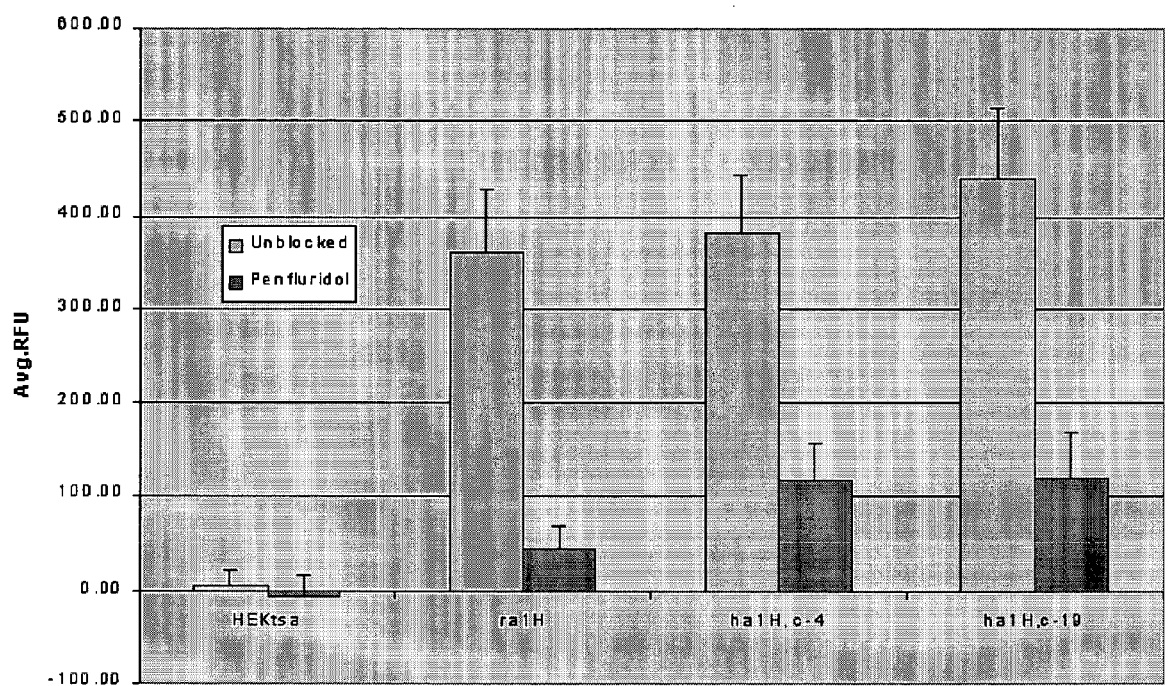
FIG. 5 shows the results of the assay of FIG. 4 in the presence and absence of a known T-type calcium channel blocker.

Then, to each well, at 15 µl/well, a solution of 15 µg/ml gramicidin in EB buffer is added over about 2 minutes. This is followed by addition of 20 µl of 60 mM KCl in MKH buffer added to each well, one well at a time. After 2 seconds excitation fluorescence was read. The results for controls are shown in FIG. 5. As shown, various concentrations of penfluoridol were successful in blocking calcium ion transport.

Buffer Compositions:

MKH buffer: 118 mM NaCl, 4.7 mM KCl, 0.5 mM $MgSO_4$, 1.2 mM $KH_2PO_4$, 11.7 mM Glucose, 2 mM $CaCl_2$, 18.4 mM HEPES, pH 7.2 (with NaOH).

EB buffer: 140 mM NMDG (pH 9.0 with HCl), 2 mM KCl, 1 mM $MgCl_2$, 5 mM Glucose, 1 mM $CaCl_2$, 16 mM HEPES, pH 7.4 (with HCl).

The invention claimed is:

1. A method to detect the activation of T-type calcium ion channels, which method comprises
    treating cells that express at least the $\alpha_1$ subunit of a T-type calcium ion channel with sufficient potassium ion to activate said T-type channel, and
    measuring the fluorescence emitted by such cells,
    wherein the cells have been modified to contain a fluorophore having an intensity of emission that changes in the presence of calcium ion, and
    wherein said cells have been treated, prior to treating with potassium ion to activate said T-type channel, with a monovalent cation-selective pore-forming substance that permits the influx and efflux of singly charged cations so as to create a cation-selective pore in the presence of a solution comprising at least one osmolality balancing component that does not permeate said pore,
    wherein said solution is an isotonic solution prepared by substituting said at least one osmolality balancing component for sodium ions,
    wherein enhancement of the intensity of fluorescence emission indicates the activation of said T-type calcium ion channels.

2. The method of claim 1, wherein the intensity of emission of said fluorophore is enhanced in the presence of calcium ion.

3. The method of claim 1, wherein the monovalent cation selective pore-forming substance is selected from the group consisting of gramicidin, artificial ion channels, and bacterial toxins.

4. The method of claim 1, wherein the osmolality balancing component comprises one or more of N-methyl-D-Glucamine (NMDG), choline, tris [hydroxymethyl] aminomethane (TRIS) and tetra-ethyl-ammonium (TEA).

5. A method to detect the activation of T-type calcium ion channels, which method comprises
    (a) treating cells that express at least the $\alpha_1$ subunit of a T-type calcium ion channel with a monovalent cation-selective pore-forming substance other than a potassium-selective ion channel so as to create a cation-selective pore in the presence of a solution comprising at least one osmolality balancing component that does not permeate said pore,
    wherein said solution is an isotonic solution prepared by substituting said at least one osmolality balancing component for sodium ions, and
    whereby the membrane potential of said cells becomes sufficiently negative to convert inactivated T-type channels to the resting state; followed by
    (b) increasing the potassium ion concentration external to said cells so as to depolarize said cell membranes sufficiently to activate the T-type channels; and
    (c) measuring the fluorescence emitted by the cells, wherein the cells have been modified to contain a fluorophore having an intensity of emission that changes in the presence of calcium ion,
    wherein enhancement of the intensity of fluorescence emission indicates activation of said T-type calcium ion channels.

6. The method of claim 5, wherein the intensity of emission of said fluorophore is enhanced in the presence of calcium ion.

7. The method of claim 5, wherein the monovalent cation selective pore-forming substance is selected from the group consisting of gramicidin, artificial ion channels, and bacterial toxins.

8. The method of claim 5, wherein the osmolality balancing component comprises one or more of N-methyl-D-Glucamine (NMDG), choline, tris [hydroxymethyl] aminomethane (TRIS) and tetra-ethyl-ammonium (TEA).

9. The method of claim 7, wherein the cation selective pore-forming substance is gramicidin.

10. The method of claim 7, wherein the monovalent cation-selective pore-forming substance is an artificial ion channel comprising a cyclic peptide containing unnatural amino acids.

11. The method of claim 7, wherein the bacterial toxin is *Clostridium perfringens* beta toxin.

12. The method of claim 7, wherein the osmolality balancing component comprises one or more of N-methyl-D-Glucamine (NMDG), choline, tris [hydroxymethyl]aminomethane (TRIS) and tetra-ethyl-ammonium (TEA).

13. The method of claim 12, wherein the osmolality balancing component is NMDG or choline.

14. The method of claim 12, wherein the osmolality balancing component is choline.

15. A method to detect the activation of T-type calcium ion channels, which method comprises
    (a) providing cells that express at least the $\alpha_1$ subunit of a T-type calcium ion channel and which have been recombinantly modified to coexpress a potassium-selective ion channel, and wherein said cells have been modified to contain a fluorophore having an intensity of emission that changes in the presence of calcium ion;

(b) maintaining the potassium ion concentration external to said cells at a level so as to obtain a negative membrane potential sufficient to convert inactivated T-type channels to the resting state; followed by (c) increasing the potassium ion concentration external to the cells to depolarize the cell membranes sufficiently to activate said T-type calcium ion channels; and (d) measuring the excitation fluorescence emitted by the fluorophore in said cells; wherein enhancement of the intensity of fluorescence emission indicates activation of the T-type calcium ion channels.

16. The method of claim 15, wherein the potassium-selective ion channel is IRK-1, TASK-1, TASK-3, TREK-1, TREK-2 or TRAAK.

17. The method of claim 15, wherein the intensity of the excitation fluorescence of said fluorophore is enhanced in the presence of calcium ion.

18. The method of claim 16, wherein the intensity of the excitation fluorescence of said fluorophore is enhanced in the presence of calcium ion.

* * * * *